United States Patent [19]

Wright

[11] 4,216,327
[45] Aug. 5, 1980

[54] 2-(2-ACETYLHYDRAZINO)-4-NITROPYRIDINE 1-OXIDE

[75] Inventor: George C. Wright, Norwich, N.Y.

[73] Assignee: Morton-Norwich Products, Inc., Norwich, N.Y.

[21] Appl. No.: 56,023

[22] Filed: Jul. 9, 1979

[51] Int. Cl.$^2$ .......................................... C07D 213/89
[52] U.S. Cl. .................................................... 546/306
[58] Field of Search ........................................ 546/306

[56] References Cited

U.S. PATENT DOCUMENTS 4,151,162  4/1979  Lang et al. ........................... 544/306

Primary Examiner—John M. Ford
Attorney, Agent, or Firm—Anthony J. Franze

[57] ABSTRACT 2-(2-Acetylhydrazino)-4-nitropyridine 1-oxide is a useful antibacterial agent.

1 Claim, No Drawings

2-(2-ACETYLHYDRAZINO)-4-NITROPYRIDINE 1-OXIDE

This invention is concerned with the chemical compound 2-(2-acetylhydrazino)-4-nitropyridine-1-oxide. It is a useful antibacterial agent particularly in the therapy of urinary tract infection due to its appearance in the urine of the host to whom it is administered. Thus when administered perorally and intraperitoneally simultaneously to rats in a dose of 50 mg/kg by each route in a vehicle of 1% sodium carboxymethylcellulose, the urine from said rats possesses antibacterial activity in respect of *Escherichia coli*, *Staphylococcus aureus* and *Proteus mirabilis*, all of which are well-known urinary tract pathogens.

The compound of this invention can be formulated in a variety of dosage forms such as tablets, elixirs, suspensions and capsules to provide readily administrable compositions.

The method currently preferred for the compound of this invention is described in the following example:

To a solution of 99 g (0.47 mole) of 2-bromopyridine 1-oxide in 133 ml of $H_2SO_4$ was added a mixture of 223 ml of $H_2SO_4$ and 116 ml of fuming $HNO_3$ (d. 1.5) at room temperature over 0.1 hour, with stirring. The reaction mixture was heated on a steam bath for 8 hours, transferred to a 6 l battery jar and neutralized (pH ca 8) at 25°–30° with 950 g (7.7 mole) of $Na_2CO_3.H_2O$, accompanied by hand stirring. The yellow crystalline mass was extracted with five 1 l portions of benzene. The benzene extracts were combined, dried over $MgSO_4$ overnight and filtered. The filtrate was concentrated to a volume of 200 ml, cooled with a cold water bath, and filtered. The pale yellow solid was washed with 100 ml of cold benzene, 300 ml of ether and air dried, m.p. 144°–146°. Yield: 69 g (68%).

To a mixture of the above described 2-bromo-4-nitropyridine 1-oxide (69 g, 0.82 mole) and 518 ml of methanol was added acetic acid hydrazide (98 g, 1.32 mole) with mechanical stirring. The reaction mixture was refluxed using a steam bath for 24 hours, stored for two days at room temperature and filtered. The yellow solid was washed with ether and air dried, m.p. 146°–150° dec. (140 sinter). Yield: 24.5 g (36%).

A 10 g portion of the crude product was washed, stirred for 4 hours with 200 ml of methanol, and filtered. The bright yellow solid was air dried, m.p. 203°–204° dec. Yield: 6 g (22%).

Anal. Calcd. for $C_7H_8N_4O_4$: C, 39.62; H, 3.80; N, 26.41. Found: C, 39.66; H, 3.84; N, 26.23.

What is claimed is:

1. The compound 2-(2-acetylhydrazino)-4-nitropyridine 1-oxide.

* * * * *